United States Patent
Miyazaki et al.

(10) Patent No.: US 8,884,226 B2
(45) Date of Patent: Nov. 11, 2014

(54) OCT DEVICE

(75) Inventors: Yasuhito Miyazaki, Hamamatsu (JP);
Yasuhito Yoneta, Hamamatsu (JP);
Hisanori Suzuki, Hamamatsu (JP);
Masaharu Muramatsu, Hamamatsu (JP);
Toshihisa Atsumi, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 13/522,103

(22) PCT Filed: Jan. 19, 2011

(86) PCT No.: PCT/JP2011/050858
§ 371 (c)(1),
(2), (4) Date: Jul. 13, 2012

(87) PCT Pub. No.: WO2011/090067
PCT Pub. Date: Jul. 28, 2011

(65) Prior Publication Data
US 2012/0287440 A1 Nov. 15, 2012

(30) Foreign Application Priority Data
Jan. 25, 2010 (JP) ................... 2010-013220

(51) Int. Cl.
G01B 9/02 (2006.01)
G01N 21/47 (2006.01)
A61B 5/00 (2006.01)
A61B 3/12 (2006.01)

(52) U.S. Cl.
CPC .......... G01N 21/4795 (2013.01); A61B 5/0066 (2013.01); A61B 3/1225 (2013.01)
USPC ....................................... 250/338.1

(58) Field of Classification Search
CPC .............................. G01B 9/02; G01N 21/4795

USPC .......... 250/363.03, 366, 208.1, 341.8, 458.1, 250/338.1
See application file for complete search history.

(56) References Cited

U.S. PATENT DOCUMENTS

| | | | |
|---|---|---|---|
| 6,025,585 A * | 2/2000 | Holland | 250/208.1 |
| 6,495,833 B1 * | 12/2002 | Alfano et al. | 250/341.8 |
| 2007/0159639 A1 | 7/2007 | Teramura et al. | |

FOREIGN PATENT DOCUMENTS

| | | |
|---|---|---|
| JP | 2007-212428 | 8/2007 |
| JP | 2009-34480 | 2/2009 |
| JP | 2009-89792 | 4/2009 |
| JP | 2010-191 | 1/2010 |
| WO | WO 2009/153929 | 12/2009 |

* cited by examiner

Primary Examiner — David Porta
Assistant Examiner — Faye Boosalis
(74) Attorney, Agent, or Firm — Drinker Biddle & Reath LLP

(57) ABSTRACT

A photodetector of an OCT device is provided with: a silicon substrate comprised of a semiconductor of a first conductivity type, having a first principal surface and a second principal surface opposed to each other, and having a semiconductor region of a second conductivity type formed on the first principal surface side; and charge transfer electrodes provided on the first principal surface and transferring generated charges. In the silicon substrate, an accumulation layer of the first conductivity type having a higher impurity concentration than the silicon substrate is formed on the second principal surface side, and an irregular asperity is formed in a region opposed to at least the semiconductor region, in the second principal surface. The region in which the irregular asperity is formed on the second principal surface of the silicon substrate is optically exposed.

4 Claims, 6 Drawing Sheets

OCT DEVICE

TECHNICAL FIELD

The present invention relates to an OCT device.

BACKGROUND ART

OCT (Optical Coherence Tomography) devices are interferometers utilizing low-coherence light. OCT devices can detect the intensity distribution of reflected or scattered light at a position specified by a position resolution of about a coherence length in the propagation direction of the light, so as to produce a tomographic image. For example, OCT devices may be used for a diagnosis of eye, tooth, or the like. Patent Literature 1 discloses technology for using an OCT device for ophthalmic diagnosis. In the OCT device disclosed in Patent Literature 1, a light source for emitting light having a wavelength within the near-infrared region is used, and a CCD (Charge Coupled Device) imaging device is used as a photodetector for detecting light having a wavelength within the near-infrared region.

CITATION LIST

Patent Literature

Patent Literature 1: Japanese Patent Application Laid-open No. 2009-034480

SUMMARY OF INVENTION

Technical Problem

In a CCD imaging device, an inexpensive and easily-manufactured silicon substrate is generally used. However, the sensitivity of a CCD imaging device using a silicon substrate suddenly decreases in the wavelength band of 900 nm or above. Although sensitivity can be maintained at about 1,000 nm by the thinning of the silicon substrate, this may cause an etalon phenomenon. The etalon phenomenon is a phenomenon of interference between incident detection target light and light resulting from reflection of the incident detection target light on a surface opposed to an incident surface. Therefore, the etalon phenomenon affects detection characteristics in the near-infrared wavelength band.

It is an object of the present invention to provide an OCT device provided with a photodetector using a silicon substrate and having sufficient sensitivity characteristics in the near-infrared wavelength band.

Solution to Problem

An OCT device according to the present invention is one comprising: a light source outputting light; a splitting unit outputting first split light and second split light by splitting the light output from the light source; a probe unit irradiating a measurement target object with the first split light output from the splitting unit and inputting and guiding light from the measurement target object; a coupling unit inputting light guided by the probe unit and reached as sample light, inputting the second split light output from the splitting unit and reached as reference light, and multiplexing the input reference light and the input sample light, and outputting an interference light caused by multiplexing; and a photodetector detecting an intensity of the interference light output from the coupling unit, wherein the photodetector comprises: a silicon substrate comprised of a semiconductor of a first conductivity type, having a first principal surface and a second principal surface opposed to each other, and having a semiconductor region of a second conductivity type formed on the first principal surface side; and a transfer electrode part provided on the first principal surface of the silicon substrate and transferring a generated charge, wherein in the silicon substrate, an accumulation layer of the first conductivity type having a higher impurity concentration than the silicon substrate is formed on the second principal surface side and an irregular asperity is formed in a region opposed to at least the semiconductor region of the second conductivity type, in the second principal surface, and wherein the region in which the irregular asperity is formed in the second principal surface of the silicon substrate is optically exposed.

In the OCT device according to the present invention, the irregular asperity is formed in the region opposed to at least the semiconductor region of the second conductivity type, in the second principal surface of the silicon substrate of the photodetector. Therefore, interference light incident into the photodetector is reflected, scattered, or diffused by the region such that the interference light travels a long distance in the silicon substrate. This causes the interference light incident into the photodetector to be mostly absorbed in the silicon substrate, without being transmitted by the photodetector (silicon substrate). In the photodetector, therefore, the travel distance of the interference light incident into the photodetector becomes long and the distance of absorption of the photodetector light also becomes long. As a result, the sensitivity characteristic in the near-infrared wavelength band is improved.

The accumulation layer of the first conductivity type having the impurity concentration higher than that of the silicon substrate is formed on the second principal surface side of the silicon substrate. This induces recombination of unnecessary carriers generated independently of light on the second principal surface side, which can reduce dark current. The accumulation layer of the first conductivity type prevents carriers generated by the interference light near the second principal surface of the silicon substrate, from being trapped in the second principal surface. For this reason, the carriers generated by the interference light migrate efficiently to a pn junction part between the second conductivity type semiconductor region and the silicon substrate, which can improve the photodetection sensitivity of the photodetector.

In the OCT device according to the present invention, the silicon substrate may be thinned in a portion corresponding to the semiconductor region of the second conductivity type, from the second principal surface side while leaving a peripheral portion around the thinned portion. In this case, the photodetector can be obtained with respective light incident surfaces on the first principal surface and second principal surface sides of the silicon substrate.

In the OCT device according to the present invention, a thickness of the accumulation layer of the first conductivity type may be larger than a height difference of the irregular asperity. In this case, as described above, an operational effect of the accumulation layer can be ensured.

In the OCT device according to the present invention, the silicon substrate may has a thickness set to not more than a pixel pitch. In this case, it is feasible to suppress an occurrence of crosstalk between pixels.

Advantageous Effect of Invention

The present invention successfully provides an OCT device provided with the photodetector using a silicon substrate and having sufficient sensitivity characteristics in the near-infrared wavelength band.

DESCRIPTION OF EMBODIMENTS

The preferred embodiments of the present invention will be described below in detail with reference to the accompanying drawings. In the description, the same elements or elements with the same functionality will be denoted by the same reference signs, without redundant description.

Figure 1:
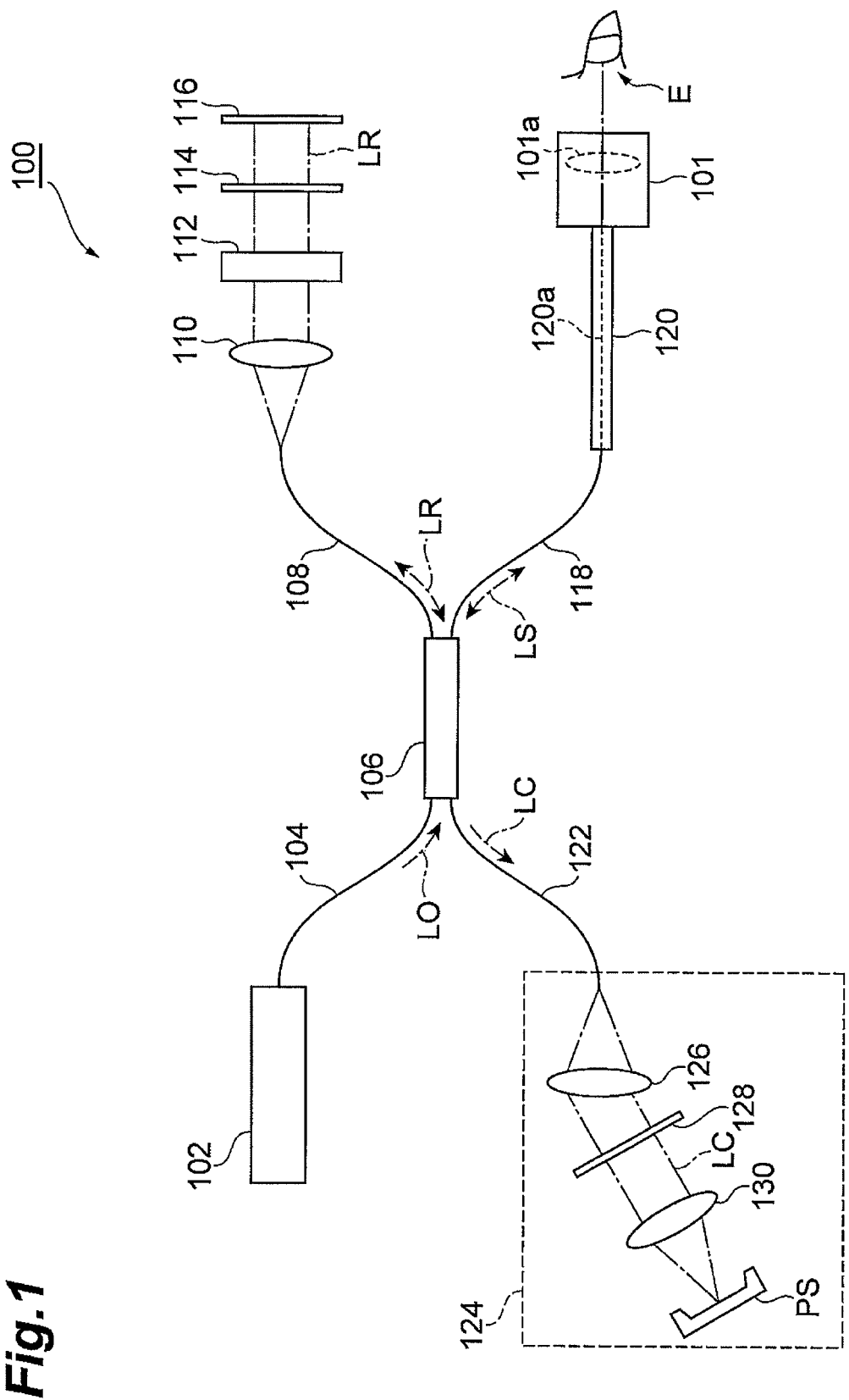
FIG. 1 is a schematic configuration diagram illustrating an OCT device.

First, with reference to FIG. 1, a configuration of an OCT device 100 will be described. FIG. 1 is a schematic configuration diagram illustrating the OCT device. For example, the OCT device 100 has a configuration for obtaining a tomographic image of a diagnosis target eye E.

The OCT device 100 splits low-coherence light into reference light and signal light, generates interference light by superimposing signal light coming via the fundus of the diagnosis target eye E and reference light traveled via a reference object, and detects the interference light. The detected result (detected signal) is input into an arithmetic and control unit (not shown). The arithmetic and control unit analyzes the detected signal to form a tomographic image of an eye-fundus (particularly, a retina).

A low-coherence light source 102 is configured by a broadband light source outputting low-coherence light LO. As the low-coherence light source 102, an SLD (Super Luminescent Diode) or LED (Light Emitted Diode) is used, for example. The low-coherence light LO includes light having wavelengths in the near-infrared region and has a temporal coherence length of several tens of micrometers (μm). The low-coherence light LO has a wavelength greater than that of illumination light (wavelength of approximately 400 nm to 800 nm) from an eye-fundus camera unit 101, and may be, for example, in the range of approximately 800 to 1,100 nm.

The low-coherence light LO output from the low-coherence light source 102 is guided to an optical coupler 106 (a splitting unit and a coupling unit) through an optical fiber 104. For example, the optical fiber 104 is comprised of a fiber such as a single mode fiber or a PM fiber (Polarization Maintaining Fiber). The optical coupler 106 splits the low-coherence light LO into reference light LR (second split light) and signal light LS (first split light). Although the optical coupler 106 functions as both a light splitter and a light coupler, the optical coupler 106 is conventionally termed an "optical coupler."

The reference light LR is guided along an optical fiber 108 and exits from a fiber end surface. The optical fiber 108 is comprised of a fiber such as a single mode fiber. The reference light LR is converted into a parallel light beam by a collimate lens 110, travels through a glass block 112 and a density filter 114, and is reflected by a reference mirror 116.

The reference light LR reflected by the reference mirror 116 travels through the density filter 114 and the glass block 112 again and is then collected by the collimate lens 110 on the fiber end surface of the optical fiber 108 so as to be guided to the optical coupler 106 along the optical fiber 108. The glass block 112 and the density filter 114 function as a delay means for matching optical path lengths (optical distances) of the reference light LR and the signal light LS, and a dispersion compensation means for matching dispersion characteristics of the reference light LR and the signal light LS.

The density filter 114 functions as a neutral density filter for reducing the amount of reference light, and for example, the density filter 114 is configured by a rotary ND (Neutral Density) filter. The amount of reference light LR reduced by the density filter 114 is varied by rotating the density filter 114 with a density filter driving mechanism (not shown). In this way, the amount of reference light LR contributing to interference light LC generation is adjusted.

The reference mirror 116 is movable in the propagation directions of the reference light LR (directions denoted by a double pointed arrow in FIG. 1). Owing to this, the length of the optical path of the reference light LR is ensured, according to the axial length of the diagnosis target eye E, a working distance (a distance between the diagnosis target eye E and an object lens 101a in the eye-fundus camera unit 101), or the like. By moving the reference mirror 116, an image can be captured at any depth of the eye-fundus. The reference mirror 116 is moved by a reference mirror driving mechanism (not shown).

The signal light LS generated by the optical coupler 106 is guided to an end of a connection line 120 by an optical fiber 118. The optical fiber 118 is comprised of a fiber such as a single mode fiber. An optical fiber 120a continues in the connection line 120. The optical fiber 118 and the optical fiber 120a may be formed of a single optical fiber or integrally formed by, for example, coupling end surfaces of the optical fibers.

The signal light LS is guided to the eye-fundus camera unit 101 (a probe unit) along the inside of the connection line 120. The signal light LS is irradiated from the eye-fundus camera unit 101 (the object lens 101a) to the diagnosis target eye E. The eye-fundus camera unit 101 is used to capture a color image, a monochrome image, or a fluorescent image from the surface of the eye-fundus. Like a conventional eye-fundus camera, the eye-fundus camera unit 101 is provided with an illumination optical system and an optical imaging system.

The signal light LS incident to the diagnosis target eye E forms an image on the eye-fundus and is reflected. At this time, the signal light LS is reflected from the surface of the eye-fundus, while the signal light LS reaches a deep region of the eye-fundus and scatters at a refractive index boundary. Therefore, after traveling via the eye-fundus, the signal light LS contains information reflecting the surface state of the eye-fundus and information reflecting the rear scattering state of the refractive index boundary of deep tissue of the eye-fundus. This light may simply be referred to as "eye-fundus reflected light of signal light LS."

The eye-fundus reflected light (sample light) of the signal light LS propagates through the eye-fundus camera unit 101 in an opposite direction of the above-mentioned pathway, is collected on an end surface of the optical fiber 120a and returns to the optical coupler 106 through the connection line 120 and the optical fiber 118.

The optical coupler 106 generates interference light LC by multiplexing the signal light LS returned via the diagnosis target eye E and the reference light LR reflected by the reference mirror 116. The interference light LC is guided to a spectrometer 124 through an optical fiber 122. The optical fiber 122 is comprised of a fiber such as a single mode fiber. Although a Michelson-type interferometer is used in the present embodiment, any type of interferometer such as a Mach-Zehnder type interferometer may be used.

The spectrometer 124 includes a collimator lens 126, a diffraction grating 128, an imaging lens 130, and a photodetector PS. The diffraction grating 128 may be a transmission type diffraction grating capable of transmitting light or a reflection type diffraction grating capable of reflecting light.

The interference light LC incident to the spectrometer 124 is converted into a parallel light beam by the collimator lens 126 and is spectrally separated (is broken into a spectrum) by the diffraction grating 128. The spectrally separated interference light LC is formed into an image on an imaging surface of the photodetector PS by the imaging lens 130. The photodetector PS detects the respective spectra of the spectrally separated interference light LC, converts the spectra into electric signals, and outputs the detected signals to an arithmetic and control unit (not shown). The detected signals correspond to the intensities of the respective spectra of the spectrally separated interference light LC. The arithmetic and control unit analyzes the detected signals input from the photodetector of the OCT device 100 to form a tomographic image of the eye-fundus of the diagnosis target eye E.

Figure 2:
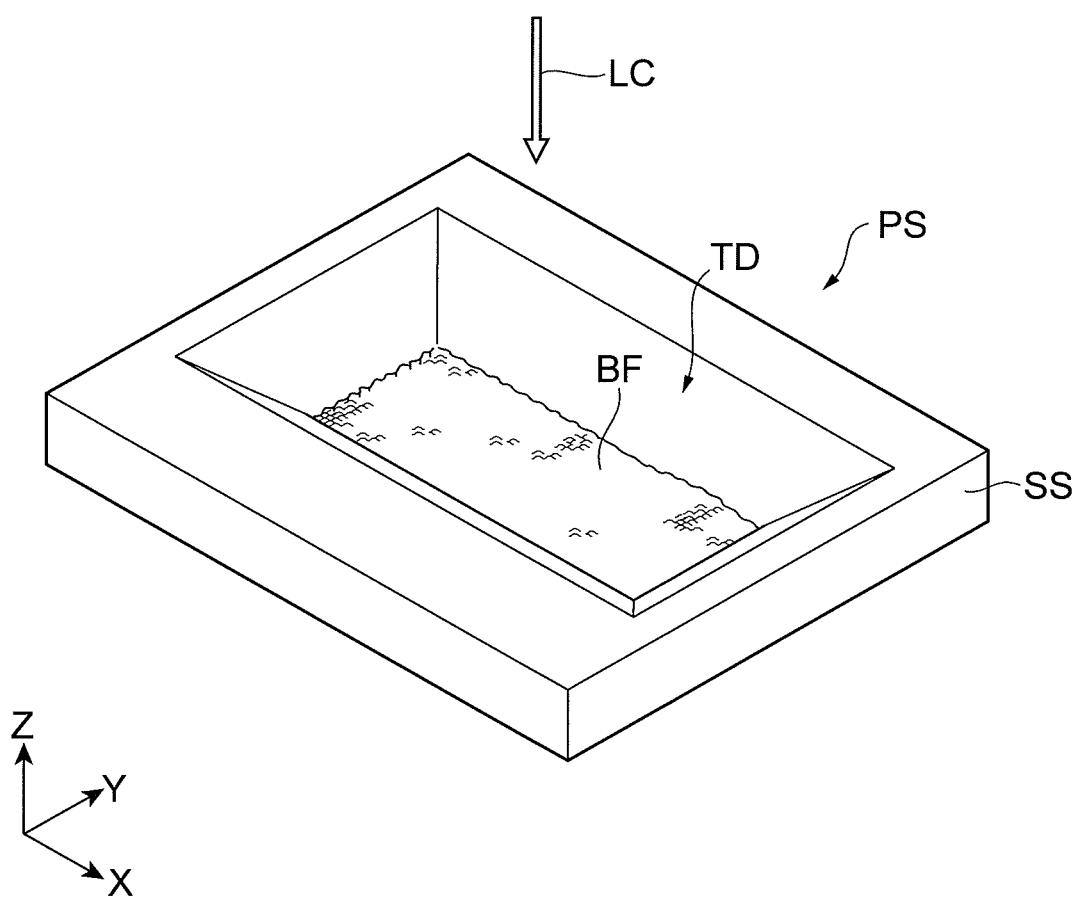
FIG. 2 is a perspective view illustrating a photodetector.
Figure 3:
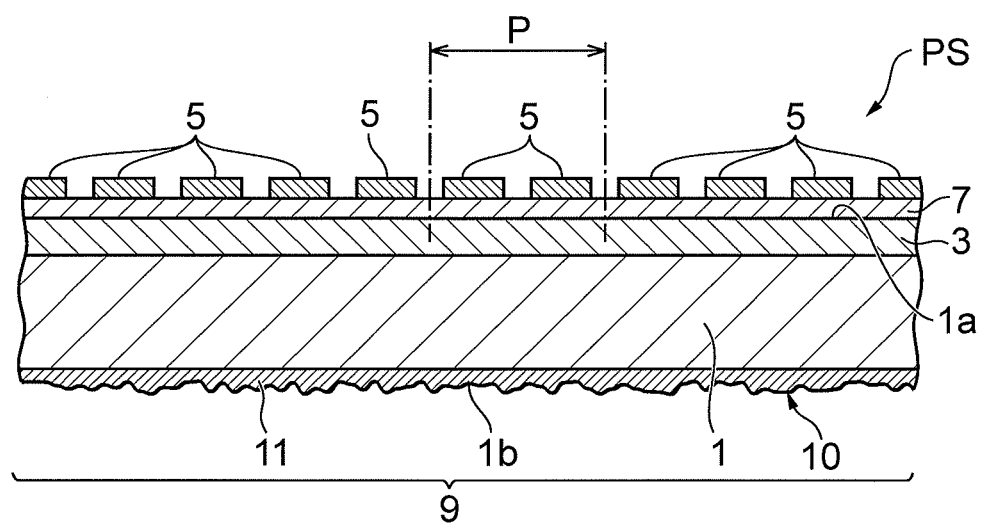
FIG. 3 is a drawing for explaining a cross-sectional configuration of the photodetector.

Next, the photodetector PS will be described with reference to FIGS. 2 and 3. FIG. 2 is a perspective view illustrating the photodetector. FIG. 3 is a drawing for explaining a cross-sectional configuration of the photodetector.

As shown in FIG. 2, the photodetector PS is a back incident type solid-state imaging device and a BT-CCD (Charge Coupled Device) obtained by thinning the back side of a semiconductor substrate SS by etching with a KOH aqueous solution or the like. A recess portion TD is formed in a central region of the etched semiconductor substrate SS, and a thick frame portion exists around the recess portion TD. Side faces of the recess portion TD are inclined at obtuse angles relative to a bottom face BF. The thinned central region of the semiconductor substrate SS is a photosensitive region (imaging region). Interference light LC is incident to the photosensitive region in the negative direction of the Z-axis. The bottom face BF of the recess portion TD of the semiconductor substrate SS constitutes a light incident surface. The photodetector PS may be provided as a back incident type solid-state imaging device the entire region of which is thinned.

The photodetector PS is provided with a p-type semiconductor substrate 1 as the foregoing semiconductor substrate SS. The p-type semiconductor substrate 1 is comprised of silicon (Si) crystal, and has a first principal surface 1a and a second principal surface 1b opposed to each other. The p-type semiconductor substrate 1 has a thickness set to not more than the pitch P of pixels. In the present embodiment, the pixel pitch P is about 10 to 48 μm, and the thickness of the p-type semiconductor substrate 1 is about 10 to 30 μm. In the present embodiment, two-phase clock driving is shown as an example and regions (not shown) of different impurity concentrations are formed under each transfer electrode in order to ensure unidirectional charge transfer.

An n-type semiconductor layer 3 as a charge transfer part is formed on the first principal surface 1a side of the p-type semiconductor substrate 1, and therefore a pn junction is formed between the p-type semiconductor substrate 1 and the n-type semiconductor layer 3. A plurality of charge transfer electrodes 5 as a transfer electrode part are provided through an insulating layer 7 on the first principal surface 1a of the p-type semiconductor substrate 1. On the first principal surface 1a side of the p-type semiconductor substrate 1, isolation regions for electrically separating the n-type semiconductor layer 3 into regions for respective vertical CCDs are also formed though not shown. The n-type semiconductor layer 3 has a thickness of about 0.5 μm.

An irregular asperity 10 is formed throughout the entire photosensitive region 9 in the second principal surface 1b of the p-type semiconductor substrate 1. An accumulation layer 11 is formed on the second principal surface 1b side of the p-type semiconductor substrate 1, and the second principal surface 1b is optically exposed. That the second principal surface 1b is optically exposed embraces not only the case in which the second principal surface 1b is in contact with ambient gas such as air, but also the case in which an optically transparent film is formed on the second principal surface 1b. If the photodetector PS is a back incident type solid-state imaging device wherein the entire region is thinned, the irregular asperity 10 may be formed throughout the entire area of the second principal surface 1b of the p-type semiconductor substrate 1. If the photodetector PS is a back incident type solid-state imaging device wherein only the region near the photosensitive region 9 is thinned, the irregular asperity 10 may be formed throughout the entire area of the second principal surface 1b including the peripheral frame portion not thinned in the p-type semiconductor substrate 1 and the inclined side faces connected to the frame portion.

Figure 4:
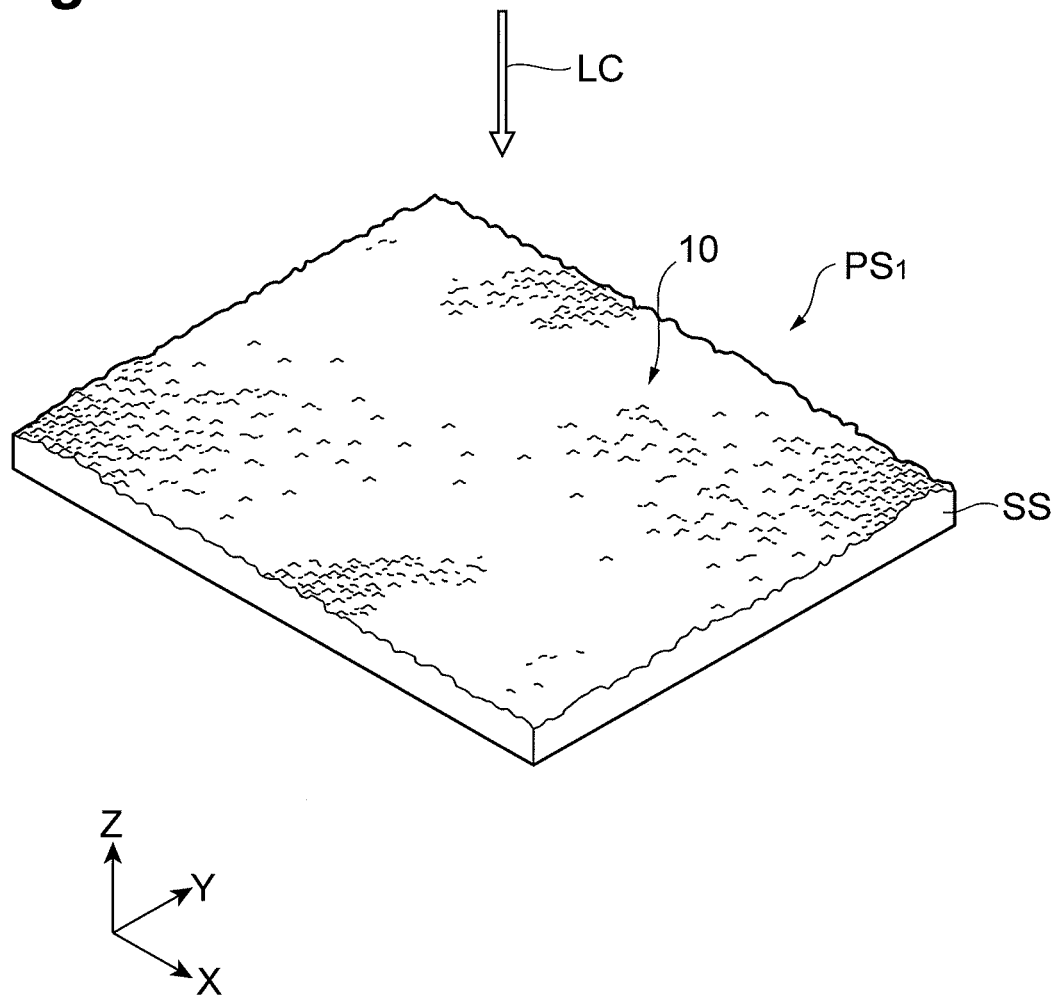
FIG. 4 is a perspective drawing illustrating a modification example of the photodetector.

The back incident type solid-state imaging device wherein the entire region is thinned may be obtained without forming no frame portion by gluing a further substrate to the front side of the semiconductor substrate SS and then polishing the back side of the semiconductor substrate SS. As shown in FIG. 4, a photodetector $PS_1$ is thinned throughout the entire back side of the semiconductor substrate SS. In the photodetector $PS_1$, an irregular asperity 10 is formed at least in a region corresponding to a photosensitive region on the back side (second principal surface) of the semiconductor substrate SS. The aforementioned accumulation layer (not shown) described above is formed on the back side of the semiconductor substrate SS.

A method for manufacturing the photodetector PS of the present embodiment will be described below.

First, an p-type semiconductor substrate 1 having a first principal surface 1a and a second principal surface 1b opposed to each other is prepared. The p-type semiconductor substrate 1 has a thickness of about 300 μm and a resistivity of about 0.001 to 10 kΩ·cm. In the present embodiment, "high impurity concentration" refers to, for example, an impurity concentration not less than about $1 \times 10^{17}$ cm$^{-3}$ and is denoted by a sign "+" attached to the conductivity type. "Low impurity concentration" refers to, for example, an impurity concentration not more than about $1 \times 10^{15}$ cm$^{-3}$ and is denoted by a sign "−" attached to the conductivity type. Examples of n-type impurities include antimony (Sb), arsenic (As), and so on, and examples of p-type impurities include boron (B) and others.

Next, an n-type semiconductor layer 3 is formed on the first principal surface 1a side of the p-type semiconductor substrate 1. The n-type semiconductor layer 3 is formed by diffusing an n-type impurity in the p-type semiconductor substrate 1 from the first principal surface 1a side.

Next, the p-type semiconductor substrate 1 is thinned from the second principal surface 1b side as described above.

Next, an accumulation layer 11 is formed on the second principal surface 1b side of the p-type semiconductor substrate 1. Like in the above-described embodiment, the accumulation layer 11 is formed by ion implantation or diffusion of a p-type impurity from the second principal surface 1b side in the p-type semiconductor substrate 1 so that the impurity concentration thereof becomes higher than that of the p-type semiconductor substrate 1. The accumulation layer 11 has a thickness of, for example, about 0.5 μm. The accumulation layer 11 may be formed before or after an irregular asperity 10 is formed.

Next, the p-type semiconductor substrate 1 is heat-treated to activate the accumulation layer 11. The heat treatment is carried out, for example, under an ambiance such as $N_2$ gas in the temperature range of about 800 to 1,000° C. for about 0.5 to 1.0 hour. At this time, the crystallinity of the p-type semiconductor substrate 1 is also restored.

Figure 5:
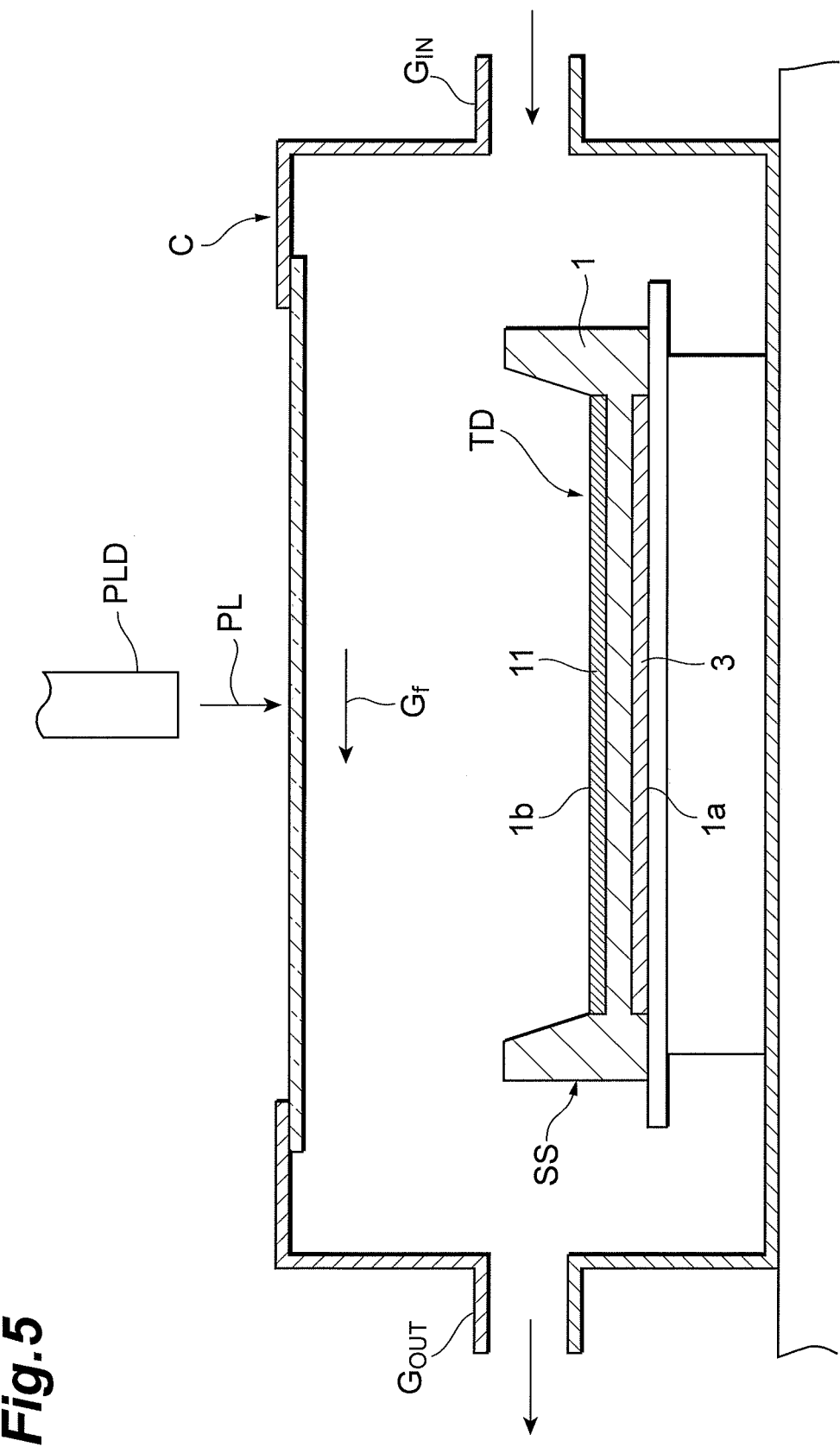
FIG. 5 is a drawing for explaining a method for manufacturing the photodetector.

Next, the second principal surface 1b of the p-type semiconductor substrate 1 is irradiated with a pulsed laser beam PL, thereby forming an irregular asperity 10. Here, as shown in FIG. 5, the p-type semiconductor substrate 1 is placed in a chamber C, and the p-type semiconductor substrate 1 is irradiated with the pulsed laser beam PL from a pulse laser generating device PLD, located outside the chamber C. The chamber C has a gas inlet port $G_{IN}$ and a gas outlet port $G_{OUT}$. An inert gas (e.g., nitrogen gas, argon gas, or the like) is introduced through the gas inlet port $G_{IN}$ and discharged through the gas outlet port $G_{OUT}$, thereby forming an inert gas flow $G_f$ in the chamber C. Dust and other materials generated during the irradiation with the pulsed laser beam PL are discharged to the outside of the chamber C by the inert gas flow $G_f$, thereby preventing processing debris, dust, and other materials from being attached to the p-type semiconductor substrate 1.

Figure 6:
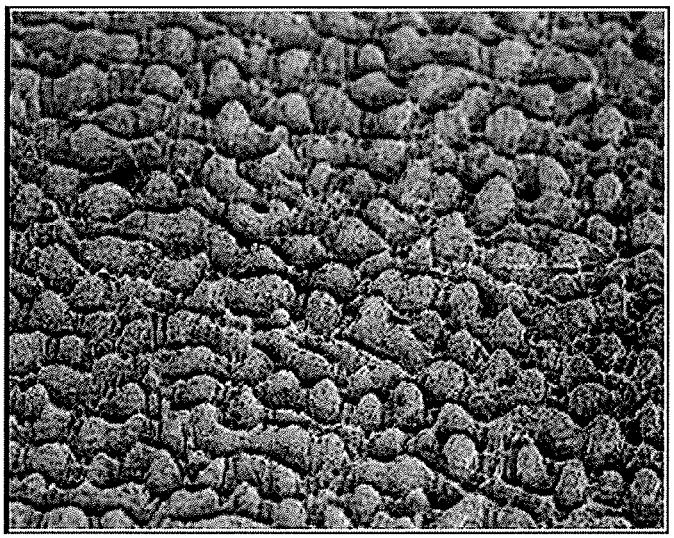
FIG. 6 is an SEM image showing irregular asperities formed in a p-type semiconductor substrate.

In the present embodiment, a picosecond to femtosecond pulse laser generating device is used as the pulse laser generating device PLD, and a picosecond to femtosecond pulsed laser beam is applied across the entire area of the second principal surface 1b. The second principal surface 1b is roughened by the picosecond to femtosecond pulsed laser beam, and thus the irregular asperity 10 is formed on the entire area of the second principal surface 1b as shown in FIG. 6. The irregular asperity 10 has facets intersecting with a direction perpendicular to the first principal surface 1a. The height difference of the asperity 10 is, for example, about 0.5 to 10 μm and the spacing between projections in the asperity 10 is about 0.5 to 10 μm. The picosecond to femtosecond pulsed laser beam has a pulse duration of, for example, about 50 fs to 2 ps, an intensity of, for example, about 4 to 16 GW, and pulse energy of, for example, about 200 to 800 μJ/pulse. More generally, the peak intensity is $3 \times 10^{11}$ to $2.5 \times 10^{13}$ (W/cm$^2$) and the fluence is about 0.1 to 1.3 (J/cm$^2$). FIG. 6 is an SEM image resulting from observation of the irregular asperity 10 formed in the second principal surface 1b.

Next, the p-type semiconductor substrate 1 is heat-treated. The heat treatment is carried out, for example, under an ambiance such as $N_2$ gas in the temperature range of about 800 to 1,000° C. for about 0.5 to 1.0 hour. The thermal treatment brings about recovery of crystal defects and recrystallization in the p-type semiconductor substrate 1, which can prevent such a problem as increase in dark current. The heat treatment after the formation of the accumulation layer 11 may be omitted, while only the heat treatment after the formation of the irregular asperity 10 may be carried out.

Next, an insulating layer 7 and charge transfer electrodes 5 are formed. Since steps of forming the insulating layer 7 and the charge transfer electrodes 5 are known, descriptions thereof will be omitted. For example, the charge transfer electrodes 5 are comprised of polysilicon or metal. For example, the insulating layer 7 is comprised of $SiO_2$. A protecting film may be further formed so as to cover the insulating layer 7 and the charge transfer electrodes 5. For example, the protecting film is comprised of BPSG (Boron Phosphor Silicate Glass). In this manner, formation of the photodetector PS is completed.

In the photodetector PS, if interference light LC is incident to the light incident surface (second principal surface 1b), since the irregular asperity 10 is formed in the second principal surface 1b, the incident interference light LC is scattered by the asperity 10 to travel in various directions in the p-type semiconductor substrate 1. Light components arriving at the first principal surface 1a and others travel in various directions owing to diffusion at the asperity 10. Therefore, the light components arriving at the first principal surface 1a and others are extremely highly likely to be totally reflected by the first principal surface 1a. The light components totally reflected by the first principal surface 1a and others are repeatedly totally reflected on different faces or, reflected, scattered, or diffused on the second principal surface 21b, whereby their travel distance becomes longer. In this manner, the interference light LC incident to the photodetector PS is reflected, scattered, or diffused by the asperity 10 to travel through a long distance in the p-type semiconductor substrate 1. While the interference light LC incident to the photodetector PS travels the long distance inside the p-type semiconductor substrate 1, the interference light LC is absorbed in the p-type semiconductor substrate 1 and carriers generated by the absorbed interference light LC turn to charges at respective pixels of the n-type semiconductor layer 3 to be transferred and detected. Therefore, the photodetector PS is improved in sensitivity characteristics in the near-infrared wavelength band.

If a regular asperity is formed on the second principal surface 1b, even though light components arriving at the first principal surface 1a and side surfaces are diffused by the asperity, the light components travel in uniform directions. Therefore, the light components arriving at the first principal surface 1a and the side surfaces are less likely to be totally reflected on the first principal surface 1a and the side surfaces. This results in increase in light passing through the first principal surface 1a and the side surfaces, and through the second principal surface 1b, and thus the travel distance of the interference light LC incident into the photodetector PS must be short. Accordingly, it becomes difficult to improve the spectral sensitivity characteristic in the near-infrared wavelength band.

Because of reflection, scattering, or diffusion by the asperity 10, the photodetector PS has a risk of a reduction in resolution due to the occurrence of crosstalk between pixels. However, since the thickness of the p-type semiconductor substrate 1 is set to be equal to or less than the pitch P of the pixels, the occurrence of crosstalk between the pixels can be suppressed in the photodetector PS.

In the photodetector PS, the accumulation layer 11 is formed on the second principal surface 1b side of the p-type semiconductor substrate 1. This induces the recombination of unnecessary carriers generated independently of light on the second principal surface 1b side, which can reduce dark current. The accumulation layer 11 prevents carriers generated by light near the second principal surface 1b from being trapped in the second principal surface 1b. For this reason, carriers generated by interference light LC efficiently migrate to the pn junction, which can further improve the photodetection sensitivity of the photodetector PS.

In the present embodiment, after the formation of the accumulation layer 11, the p-type semiconductor substrate 1 is heat-treated. This restores the crystallinity of the p-type semiconductor substrate 1, which can prevent a problem such as an increase of dark current.

In the present embodiment, after the heat treatment of the p-type semiconductor substrate 1, the charge transfer electrodes 5 are formed. This prevents the charge transfer electrodes 5 from melting during the heat treatment, even in the case that the charge transfer electrodes 5 are made of a material with a relatively low melting point, and thus the charge transfer electrodes 5 can be appropriately formed without being affected by the heat treatment.

In the present embodiment, the irregular asperity 10 is formed by irradiation with a picosecond to femtosecond pulsed laser beam. This permits the irregular asperity 10 to be appropriately and readily formed.

Incidentally, in the case of a semiconductor photodetection element like a solid-state image device, it is possible to realize the solid-state imaging device with the spectral sensitivity characteristic in the near-infrared wavelength band, by setting the semiconductor substrate of silicon thick (e.g., about 200 µm). However, in the case of the semiconductor substrate having the increased thickness in order to achieve good resolution, it is necessary to apply a large bias voltage of about several tens of volts to completely deplete the semiconductor substrate. The reason for it is to prevent the following phenomenon: if the semiconductor substrate is not completely depleted and a neutral region still remains in part of the semiconductor substrate, carriers generated in the neutral region will diffuse so as to degrade the resolution.

As the semiconductor substrate becomes thicker, the dark current also increases. For this reason, it is also necessary to cool the semiconductor substrate (e.g., to −70 to −100° C.) so as to suppress an increase in dark current.

However, in the photodetector PS, since the irregular asperity 10 is formed in the second principal surface 1b as described above, the travel distance of the interference light LC incident to the photodetector PS becomes longer. For this reason, it is feasible to realize the photodetector PS with the sufficient spectral sensitivity characteristic in the near-infrared wavelength band, without need for increasing the thickness of the semiconductor substrate (p-type semiconductor substrate 1), particularly, the portion corresponding to the photosensitive region 9. Therefore, when compared to a semiconductor photodetection element having spectral sensitivity characteristics in the near-infrared wavelength band based on an increase in the thickness of a semiconductor substrate, the aforementioned photodetector PS can provide good resolution with application of an extremely lower bias voltage or without application of any bias voltage. In addition, it may be unnecessary to cool the semiconductor substrate according to use applications.

When the semiconductor substrate, particularly the portion corresponding to the photosensitive region, is thinned, there is a risk of occurrence of an etalon phenomenon. The etalon phenomenon is a phenomenon in which detection target light incident from the back surface interferes with light resulting from reflection of the incident detection target light at the front surface, and affects detection characteristics in the near-infrared wavelength band. In the photodetector PS, however, since the irregular asperity 10 is formed on the second principal surface 1b, light reflected by the asperity 10 has dispersed phase differences relative to the phase of incident light. As a result, these lights cancel each other, thereby suppressing the etalon phenomenon.

In the present embodiment, the p-type semiconductor substrate 1 is thinned from the second principal surface 1b side. This allows the semiconductor photodetection element to be formed with respective light incident surfaces on the first principal surface 1a and second principal surface 1b sides of the p-type semiconductor substrate 1. Namely, the photodetector PS can also be used as a front incident type solid-state imaging device as well as a back incident type solid-state imaging device.

In the case where the irregular asperity 10 is formed by irradiation with a pulsed laser beam after the accumulation layer 11 is formed, it is preferable that the thickness of the accumulation layer 11 is set larger than the height difference of the irregular asperity 10. In this case, the accumulation layer 11 remains with certainty even after the irregular asperity 10 is formed by irradiation with a pulsed laser beam. Therefore, it is feasible to ensure an operational effect of the accumulation layer 11.

The above described the preferred embodiments of the present invention, but it should be noted that the present invention is not always limited to the above-described embodiments and that the present invention can be modified in many ways without departing from the spirit and scope of the invention.

In the photodetector PS of the above-described embodiments, the conductivity types of p type and n type may be interchanged so as to be reverse to those described above.

Industrial Applicability

The present invention is applicable to OCT devices for ophthalmic diagnosis, dental diagnosis, or the like.

List of Reference Signs

1 . . . p-type semiconductor substrate; 1a . . . first principal surface; 1b . . . second principal surface; 3 . . . n-type semiconductor layer; 5 . . . charge transfer electrodes; 7 . . . insulating layer; 9 . . . photosensitive region; 10 . . . irregular asperity; 11 . . . accumulation layer; 100 . . . OCT device; 101 . . . eye-fundus camera unit; 102 . . . low-coherence light source; 106 . . . optical coupler; 116 . . . reference mirror; 124 . . . spectrometer; E . . . diagnosis target eye; PS, $PS_1$ . . . photodetector; SS . . . semiconductor substrate; TD . . . recess portion.

The invention claimed is:

1. An OCT device comprising:
a light source outputting light;
a splitting unit outputting first split light and second split light by splitting the light output from the light source;
a probe unit irradiating a measurement target object with the first split light output from the splitting unit and inputting and guiding light from the measurement target object;
a coupling unit inputting light guided by the probe unit and reached as sample light, inputting the second split light output from the splitting unit and reached as reference light, and multiplexing the input reference light and the input sample light, and outputting an interference light caused by multiplexing; and
a photodetector detecting an intensity of the interference light output from the coupling unit,
wherein the photo detector comprises:
a silicon substrate comprised of a semiconductor of a first conductivity type, having a first principal surface and a second principal surface opposed to each other, and having a semiconductor region of a second conductivity type formed on the first principal surface side; and
a transfer electrode part provided on the first principal surface of the silicon substrate and transferring a generated charge,
wherein in the silicon substrate, an accumulation layer of the first conductivity type having a higher impurity concentration than the silicon substrate is formed on the second principal surface side and an irregular asperity is formed in a region opposed to at least the semiconductor region of the second conductivity type, in the second principal surface, and
wherein the region in which the irregular asperity is formed in the second principal surface of the silicon substrate is optically exposed.

2. The OCT device according to claim 1,
wherein the silicon substrate is thinned in a portion corresponding to the semiconductor region of the second conductivity type, from the second principal surface side while leaving a peripheral portion around the thinned portion.

3. The OCT device according to claim 1, wherein a thickness of the accumulation layer of the first conductivity type is larger than a height difference of the irregular asperity.

4. The OCT device according to claim 1, wherein the silicon substrate has a thickness set to not more than a pixel pitch.

* * * * *